United States Patent
Oftring et al.

(10) Patent No.: US 8,153,845 B2
(45) Date of Patent: *Apr. 10, 2012

(54) METHOD FOR PRODUCING AMINONITRILES

(75) Inventors: Alfred Oftring, Bad Dürkheim (DE); Kirsten Dahmen, Freinsheim (DE); Thilo Hahn, Kirchheimbolanden (DE); Randolf Hugo, Dirmstein (DE); Katrin Baumann, Mannheim (DE); Johann-Peter Melder, Böhl-Iggelheim (DE)

(73) Assignee: BASF SE (DE)

( * ) Notice: Subject to any disclaimer, the term of this patent is extended or adjusted under 35 U.S.C. 154(b) by 73 days.

This patent is subject to a terminal disclaimer.

(21) Appl. No.: 12/529,096

(22) PCT Filed: Feb. 28, 2008

(86) PCT No.: PCT/EP2008/052412
§ 371 (c)(1),
(2), (4) Date: Aug. 28, 2009

(87) PCT Pub. No.: WO2008/104581
PCT Pub. Date: Sep. 4, 2008

(65) Prior Publication Data
US 2010/0016625 A1    Jan. 21, 2010

(30) Foreign Application Priority Data
Mar. 1, 2007    (EP) .................................. 07103285

(51) Int. Cl.
C07C 209/48    (2006.01)
(52) U.S. Cl. ........................................ 564/490; 564/491
(58) Field of Classification Search .................. 558/302; 564/490, 491
See application file for complete search history.

(56) References Cited

U.S. PATENT DOCUMENTS

| | | | |
|---|---|---|---|
| 2,511,487 A | 6/1950 | Thompson | |
| 3,988,360 A | 10/1976 | Gaudette et al. | |
| 4,404,167 A | 9/1983 | Rozenfeld et al. | |
| 4,895,971 A | 1/1990 | Su et al. | |
| 5,079,380 A | 1/1992 | Thunberg | |
| 6,469,211 B2 | 10/2002 | Ansmann et al. | |
| 7,880,035 B2 * | 2/2011 | Oftring et al. ................ | 564/490 |

FOREIGN PATENT DOCUMENTS

| | | |
|---|---|---|
| EP | 0426394 A1 | 5/1991 |
| EP | 1209146 A1 | 5/2002 |

OTHER PUBLICATIONS

Nishimura, Shigeo, "Handbook of Heterogeneous Catalytic Hydrogenation for Organic Synthesis", (2001) pp. 213-215.
Malveda, Michael P "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,101, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,079, filed Aug. 28, 2009.
U.S. Appl. No. 12/529,087, filed Aug. 28, 2009.
U.S. Appl. No. 12/529,107, filed Aug. 28, 2009.

* cited by examiner

*Primary Examiner* — Kamal Saeed
*Assistant Examiner* — Kristin Bianchi
(74) *Attorney, Agent, or Firm* — Connolly Bove Lodge & Hutz LLP

(57) ABSTRACT

The invention relates to a process for preparing an amino nitrile mixture comprising aminoacetonitrile (AAN) and from 5 to 70% by weight of iminodiacetonitrile (IDAN), which comprises heating crude AAN which is largely free of formaldehyde cyanohydrin (FACH-free) at a temperature of from 50 to 150° C.

10 Claims, No Drawings

METHOD FOR PRODUCING AMINONITRILES

CROSS-REFERENCE TO RELATED APPLICATIONS

This application is a national stage application (under 35 U.S.C. §371) of PCT/EP2008/052412, filed Feb. 28, 2008, which claims benefit of European application 07103285.8, filed Mar. 1, 2007.

BACKGROUND OF THE INVENTION

The invention relates to a process for preparing an amino nitrile mixture comprising aminoacetonitrile (AAN) and from 5 to 70% by weight of iminodiacetonitrile (IDAN).

AAN and IDAN are important starting materials or intermediates in the preparation of ethylene amines by catalytic hydrogenation. Thus, for example, EP-A 1 209 146 relates to a process for the continuous hydrogenation of nitrites to primary amines, with ethylenediamine (EDA) being prepared from AAN as starting material and diethylenetriamine (DETA) being prepared from IDAN as starting material.

Processes for preparing AAN and IDAN are likewise known. Thus, U.S. Pat. No. 5,079,380 relates to a process for preparing AAN, in which ammonia ($NH_3$), formaldehyde (HCHO) and hydrocyanic acid (HCN) are reacted at least 100° C. Furthermore, it is generally known that as an alternative formaldehyde and hydrocyanic acid can firstly be reacted to form formaldehyde cyanohydrin (FACH) as intermediate which subsequently reacts further with ammonia to form AAN. The molar ratio of ammonia to FACH or to formaldehyde and hydrocyanic acid is usually 4:1 [mol/mol]. The temperatures in the AAN synthesis are from 50 to 80° C. and the pH is about 10. The preparation of IDAN likewise usually starts out from ammonia and FACH or ammonia, formaldehyde and hydrocyanic acid. The reaction to form IDAN is generally carried out at higher temperatures (about 100-150° C.), a lower pH of about 5-7 and a smaller proportion of ammonia than in the corresponding synthesis of AAN. Such processes for preparing IDAN are described, for example, in EP-A 426 394 or U.S. Pat. No. 4,895,971. As an alternative, the preparation of IDAN can also be carried out by reacting urotropin (hexamethylenetetraamine; HMTA) with hydrocyanic acid and formaldehyde, as described, for example, in U.S. Pat. No. 3,988,360.

U.S. Pat. No. 2,511,487 relates to a process in which IDAN is prepared from AAN. Here, AAN is mixed with FACH in a molar ratio of about 1:0.3-1.5 [mol/mol] and heated at from 100 to 150° C. in the presence of a mineral acid stabilizer such as phosphoric acid. To obtain a very high yield of IDAN, the reaction preferably takes place at from 135 to 150° C. for a maximum of 15 minutes. However, U.S. Pat. No. 2,511,487 does not mention that the mixture of AAN and FACH is passed through a (separate) apparatus; rather, the reaction takes place in a customary flask provided with cooling facilities.

In all the above-described processes for preparing AAN or IDAN, attempts are always made to prepare the respective product (AAN or IDAN) in a very high purity. However, processes in which an amino nitrile mixture comprising mainly (as amino nitrites) AAN and IDAN in a defined composition can be prepared deliberately are not known. To prepare such an amino nitrile mixture comprising AAN and IDAN, it is in principle possible to mix the two main components AAN and IDAN in the desired ratio. However, disadvantages of this method are that, firstly, two separate materials (AAN and IDAN) have to be employed and, secondly, the isolation and handling of the IDAN which is obtained as a solid frequently presents problems.

BRIEF SUMMARY OF THE INVENTION

It is therefore an object of the invention to provide an improved process for preparing an amino nitrile mixture which comprises defined amounts of AAN and IDAN, with the proportion of IDAN in the mixture being able to be varied. Here, the total amount of IDAN comprised in the amino nitrile mixture should be from 5 to 70% by weight, based on the total amount of amino nitrites comprised in the mixture.

According to the invention, this object is achieved by a process for preparing an amino nitrile mixture comprising aminoacetonitrile (AAN) and from 5 to 70% by weight of iminodiacetonitrile (IDAN), which comprises heating crude AAN which is largely free of formaldehyde cyanohydrin (FACH-free) at a temperature of from 50 to 150° C.

DETAILED DESCRIPTION OF THE INVENTION

The process of the invention has the advantage that an amino nitrile mixture comprising defined amounts of the two main constituents AAN and IDAN can be prepared. Moreover, a mixture comprising AAN and from 5 to 70% by weight of IDAN can be prepared in a very selective way. The process of the invention thus allows a varying IDAN content in the amino nitrile mixture to be set. This is achieved in a simple way since only one starting material (AAN) has to be prepared and IDAN is formed from part of this, once again within the process of the invention.

In contrast to the process described in U.S. Pat. No. 2,511,487, in which complete conversion of AAN into IDAN (by means of FACH) is sought, no additional FACH is added in the process of the invention. In this way, it is possible to prepare amino nitrile mixtures having a variable proportion of IDAN. A separate preparation of IDAN is likewise unnecessary and the associated problems of isolation and handling of the product (IDAN) obtained as a solid do not occur in the process of the invention.

As crude AAN, it is generally possible to use any type of AAN in the process of the invention. However, the crude AAN is usually in the form of an aqueous or aqueous-ammoniacal solution. The proportion of AAN in the crude AAN is normally from 5 to 100% by weight, preferably from 10 to 80% by weight.

The crude AAN is preferably prepared by reaction of an aqueous mixture of ammonia with formaldehyde cyanohydrin (FACH) in a molar ratio of ≧4:1 [mol/mol] at a temperature of from 50 to 80° C. This process is known to those skilled in the art. The reaction is preferably carried out at about 70° C. in a flow reactor at a residence time of about 10-20 minutes. The reaction is preferably carried out so that the FACH content of the crude AAN is very low. To achieve this, a sufficiently long residence time or a reaction temperature which is not too low are/is set. If appropriate, these reaction parameters are optimized so that virtually no FACH remains in the output from the reaction.

As an alternative, the crude AAN can be prepared by other methods known to those skilled in the art, for example by reaction of ammonia with formaldehyde and hydrocyanic acid.

For the purposes of the present invention, the expression "largely free of formaldehyde cyanohydrin (FACH-free)" means that not more than 10 mol % of FACH is present in the crude AAN, based on the amount of AAN. The FACH concentration in the crude AAN is preferably ≦1 mol % and particular preference is given to the crude AAN being completely FACH-free.

It can also be advantageous to remove part or all of any ammonia which has not been reacted in the preparation of the crude AAN from the crude AAN solution. The complete or partial removal of the excess ammonia is preferably effected by flash evaporation. The ammonia is preferably removed to such an extent that the molar ratio of ammonia to AAN in the crude AAN is ≦2.5:1 [mol/mol].

The process of the invention can in principle be carried out in any desired apparatus. For example, the process of the invention can be carried out in the same apparatus as the preceding synthesis of the crude AAN or the process of the invention is carried out in a separate apparatus. The process of the invention is preferably carried out in the same reactor as the synthesis of the crude AAN.

In a continuous process, it is possible to use, for example, a flow tube or a cascade of flow tubes. Each flow tube can be divided into a plurality of sections defined by the reaction conditions which prevail, so that although only one apparatus is present this corresponds in reaction engineering terms to a cascade of flow tubes. This can be achieved in practice by means of different heating or cooling zones, different catalysts or intermediate introduction of reactants or inert components (e.g. solvents). Other types of reactor can also be used individually or as a cascade. In particular, it is also possible to connect different types of reactor or apparatuses to form a cascade. Possible types of reactor are, in addition to the flow tube, loop reactors, stirred vessels, falling film evaporators, thin film evaporators or other types of heat exchangers. These apparatuses or reactors can in each case be operated with or without an external circuit, with the external circuit being able to effect backmixing or simple introduction or removal of heat via an external heat exchanger.

In particular, it is possible to carry out the synthesis of the crude AAN in the first reactor or part of a reactor or reactor section. In the second reactor or reactor part or reactor section, complete or partial removal of ammonia can then be carried out if appropriate, for example by flashing of the crude AAN stream or by distillation. In a third reactor or in the third section of the reactor or part reactor, the partial transformation of the AAN into IDAN finally takes place.

In the case of a batchwise preparation of the reaction mixture, preference is given to using a single reactor or a single apparatus in which the above-described individual steps (crude AAN preparation, $NH_3$ removal, partial conversion of AAN into IDAN) are carried out in succession. For this purpose, the reaction conditions desired for the respective substep are set in succession. Suitable types of reactor are, for example, stirred vessels, loop reactors, tanks or stirred tanks having a superposed distillation column, in each case with or without an external circuit, with the external circuit serving to regulate the temperature, or the reaction takes place completely or partly in the external heat exchanger. In a specific embodiment, it is possible to combine reaction and distillation in a continuous or discontinuous reactive distillation column.

The process of the invention is preferably carried out in an apparatus selected from among a tube reactor, a flow tube, a falling film evaporator or thin film evaporator. These reactors can be used individually or as a cascade of identical or different reactors. In particular, a reactor cascade can also be realized in a single reactor or a single apparatus by means of different reaction conditions in different sections.

If appropriate, ammonia liberated in the setting of the desired amino nitrile mixture can also be removed from the apparatus, for example by distilling off $NH_3$. Preference is given to carrying out a simultaneous removal of ammonia and synthesis of an amino nitrile mixture in a vessel or stirred vessel having a superposed distillation column or in a reactive distillation column. Furthermore, preference is given to the molar ratio of ammonia to AAN being set to a value of ≦2.5:1 [mol/mol].

In the process of the invention, the crude AAN is heated to a temperature of from 50 to 150° C., preferably from 60 to 130° C.

In a further embodiment of the present invention, the crude AAN is prepared in one apparatus and subsequently passed through a separate apparatus (A1). In this alternative embodiment, the crude AAN is heated at a temperature of from 70 to 150° C. for a maximum of 30 minutes. The temperature is preferably from 80 to 130° C. Suitable apparatuses (A1) are in principle all apparatuses through which the AAN can be passed in the temperature range indicated. The apparatus (A1) is preferably a tube reactor, a flow tube, a falling film evaporator or a thin film evaporator. These types of reactor can be operated individually or be connected to form a cascade. Reaction conditions which differ in different sections make it possible to realize a reactor cascade in a single apparatus, for example in a flow tube having different temperature zones.

In principle, amino nitrile mixtures comprising, as main components, AAN and from 5 to 70% by weight of IDAN can be prepared by means of the process of the invention. The IDAN content is preferably from 5 to 50% by weight, more preferably from 10 to 40% by weight, particularly preferably from 10 to 25% by weight. The AAN content is normally from 30 to 95% by weight, preferably from 50 to 95% by weight, particularly preferably from 75 to 90% by weight. The percentages by weight of AAN and IDAN indicated above are based on the total amount of amino nitriles comprised in the mixture. Any water, solvent or other by-products, e.g. further amino nitriles, or other impurities which may be present are not taken into account in these figures.

However, to prepare an amino nitrile mixture comprising a very high proportion of IDAN (based on the range from 5 to 70% by weight) in the process of the invention, the following parameters can be altered independently of one another:

i) A relatively high temperature is selected within the indicated temperature range from 70 to 150° C. The higher the temperature chosen, the higher the proportion of IDAN in the amino nitrile mixture;

ii) the time for which the crude AAN is heated is made long. The longer the time for which the crude AAN is exposed to an elevated temperature, the higher the proportion of IDAN in the amino nitrile mixture; or iii) the $NH_3$ content in the apparatus is reduced. The lower the $NH_3$ content in the apparatus, the higher the IDAN content of the amino nitrile mixture.

Here, an increase in temperature promotes the removal of $NH_3$ and thus leads, according to i) and iii), to a higher IDAN content. The pressure also increases with decreasing $NH_3$ content. If appropriate, the temperature can be increased further by increasing the pressure, with the pressure being applied externally, or the process is carried out at the autogenous pressure (=vapor pressure of the mixture at the given temperature).

The amino nitrile mixture obtained in the process of the invention can subsequently be processed further. The amino nitrile mixture is preferably subsequently subjected to a catalytic hydrogenation by methods known to those skilled in the art to give an ethylene amine mixture. The ethylene amine mixture obtained in the catalytic hydrogenation comprises, in particular, EDA and DETA. If appropriate, the individual components of the ethylene amine mixture obtained after the hydrogenation can be isolated; these are preferably EDA and/or DETA.

The present invention therefore further provides for the use of the amino nitrile mixture prepared using the process of the invention for preparing ethylene amine by catalytic hydrogenation, with, if appropriate, EDA and/or DETA being able to be isolated from the ethylene amine mixture.

If appropriate, the individual components of the amino nitrile mixture, in particular AAN and IDAN, can also be isolated again from the amino nitrile mixture.

The process of the invention can be carried out as a (semi) batch process or preferably a continuous process. In one embodiment of the present invention, the amino nitrile mixture is prepared directly after the synthesis of the crude AAN. In this embodiment, the crude AAN is preferably prepared by reaction of ammonia with FACH.

The invention is illustrated by the following examples. Unless indicated otherwise, all percentages are by weight (% by weight).

Example 1

Preparation of the Crude AAN

General Method:

Reaction of an aqueous mixture of ammonia with formaldehyde cyanohydrin (FACH) in a molar ratio of $\geq 4:1$ at about 70° C. in a flow reactor. Residence time: about 10 minutes. The crude AAN obtained is largely FACH-free.

The excess ammonia can be partly or completely removed from this mixture by flash evaporation.
Yield of AAN (based on FACH): $\geq 95\%$
Weight ratio of AAN: IDAN=99:1
Selectivity to AAN+IDAN: >97%
Specific Procedure:

Reaction of 243.4 g (1.742 mol) of 44.5% strength aqueous FACH with 118.6 g (6.96 mol) of liquid ammonia.

The two reactants are mixed by means of a static mixer before they enter the tube.
Tube reactor: length=400 mm, diameter=10 mm; with glass sphere packing (diameter=3 mm); volume=60 ml.

After the reaction zone, the product mixture comprises the following approximate composition:
35% of AAN, 20% of ammonia, <1% of FACH, <1% of IDAN, balance water.

Example 2

Process According to the Invention

Reaction of the aqueous-ammoniacal AAN solution prepared as described in example 1 in the flow tube:
Apparatus: as in Example 1
Molar ratio=1:1 (AAN to ammonia): about 28% by weight of AAN, about 9% of ammonia Molar ratio=1:0.5: about 37% of AAN, about 5-6% of ammonia
Molar ratio=1:1.5: about 25% of AAN, about 10-11% of ammonia
Balance: in each case water

| Experiment | Molar ratio of AAN:NH$_3$ | T (° C.) | Re. t. (min.) | Weight ratio (%) of AAN:IDAN |
|---|---|---|---|---|
| 1 | 1:1 | 100 | 20 | 79:21 |
| 2 | 1:1 | 100 | 10 | 87:13 |
| 3A | 1:0.5 | 100 | 10 | 80:20 |
| 3B | 1:0.5 | 100 | 20 | 69:31 |
| 4 | 1:1.5 | 120 | 5 | 75:25 |

Re. t.=residence time in the flow tube
Selectivity (AAN+IDAN): $\geq 98\%$ in all cases

The invention claimed is:

1. A process for preparing an amino nitrile mixture comprising aminoacetonitrile (AAN) and from 5 to 70% by weight of iminodiacetonitrile (IDAN), which comprises heating crude AAN which is largely free of formaldehyde cyanohydrin (FACH) at a temperature of from 50 to 150° C.

2. The process according to claim 1, wherein crude AAN is heated at a temperature of from 60 to 130° C.

3. The process according to claim 1, wherein the amino nitrile mixture comprises from 10 to 40% by weight of IDAN.

4. The process according to claim 1, wherein the process is carried out in a tube reactor, flow tube, falling film evaporator, thin film evaporator or a cascade of two or more of the types of reactor mentioned, with a cascade comprising identical or different reactors.

5. The process according to claim 1, wherein the molar ratio of NH$_3$ to AAN in the crude AAN is $\leq 2.5:1$ [mol/mol] and/or NH$_3$ liberated during the setting of the amino nitrile mixture is distilled off from the apparatus.

6. The process according to claim 1, wherein the crude AAN is prepared from NH$_3$ and formaldehyde cyanohydrin (FACH) in a molar ratio of $\geq 4:1$ [mol/mol] at a temperature of from 50 to 80° C.

7. The process according to claim 1 which is carried out directly after the synthesis of the crude AAN.

8. The process according to claim 1, wherein, in each case within the parameter ranges indicated,
  i. a relatively high temperature is selected,
  ii. a relatively long residence time is selected or
  iii. the NH$_3$ content in an apparatus is reduced,
in order to achieve higher proportions of IDAN in the mixture.

9. The process according to claim 1, wherein the amino nitrile mixture obtained is subsequently subjected to a catalytic hydrogenation to give an ethylene amine mixture.

10. The process according to claim 9, wherein ethylenediamine (EDA) or diethylenetriamine (DETA) is isolated from the ethylene amine mixture obtained in the hydrogenation.

* * * * *